(12) United States Patent
Thompson, Jr. et al.

(10) Patent No.: US 10,022,248 B2
(45) Date of Patent: *Jul. 17, 2018

(54) BIDIRECTIONAL BIOMECHANICAL PROSTHETIC FULL FINGER CONFIGURED FOR ABDUCTION AND ADDUCTION WITH MCP PIVOT

(71) Applicant: RCM ENTERPRISE, LLC, Turnwater, WA (US)

(72) Inventors: Robert Thompson, Jr., Olympia, WA (US); Jon Bengtsson, Olympia, WA (US); Anthony Charles Peto, Olympia, WA (US); Sydney Tye Minnis, Seattle, WA (US); Eric Dennis Klumper, Boulder, CO (US); Bradley Arthur Crittenden, Olympia, WA (US)

(73) Assignee: RCM Enterprise LLC, Olympia, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/480,088

(22) Filed: Apr. 5, 2017

(65) Prior Publication Data

US 2017/0231786 A1 Aug. 17, 2017

Related U.S. Application Data

(62) Division of application No. 15/155,801, filed on May 16, 2016, now Pat. No. 9,707,103.

(Continued)

(51) Int. Cl.
*A61F 2/54* (2006.01)
*A61F 2/58* (2006.01)
(Continued)

(52) U.S. Cl.
CPC ............. *A61F 2/586* (2013.01); *A61F 2/68* (2013.01); *A61F 2/76* (2013.01); *A61F 2/78* (2013.01);
(Continued)

(58) Field of Classification Search
CPC .... A61F 2/54; A61F 2/586; A61F 2002/7856; A61F 5/013; A61F 2/58
See application file for complete search history.

(56) References Cited

U.S. PATENT DOCUMENTS

| 319,776 A | 6/1885 | Bashore |
| 984,179 A | 2/1911 | Aydt |

(Continued)

FOREIGN PATENT DOCUMENTS

| GB | 2488365 | 8/1912 |
| GB | 110333 | 10/1917 |
| JP | 2002345861 | 12/2002 |

OTHER PUBLICATIONS

Pop, S., "Finger Prosthetic Shows Perfect Balance Between Flexibility and Sturdiness—Gallery", Oct. 23, 2014, 8 pp. as downloaded on Jul. 12, 2017.

(Continued)

*Primary Examiner* — Bruce E Snow
(74) *Attorney, Agent, or Firm* — James A. Sheridan; Sheridan Law, LLC

(57) ABSTRACT

The disclosure provides apparatus and methods of use pertaining to a bidirectional biomechanical prosthetic finger assembly. In one embodiment, the assembly includes an eccentric metacarpophalangeal (MCP) pivot configured for swivelable attachment to a hand of a user, a distal coupler, and an articulation assembly rotatively coupled therebetween. A ring configured to receive a user's residual finger is disposed upon the articulation assembly, and may be (Continued)

adjusted to a target location based on a length of the residual finger. The articulation assembly is configured to utilize vertical movements of the residual finger within the ring to articulate the distal coupler within a plane parallel to an x-z plane, and the MCP pivot is configured to utilize lateral movements of the residual finger within the ring to articulate the distal coupler within a plane parallel to an x-y plane. Other embodiments are also disclosed.

11 Claims, 11 Drawing Sheets

Related U.S. Application Data

(60) Provisional application No. 62/209,836, filed on Aug. 25, 2015, provisional application No. 62/162,516, filed on May 15, 2015.

(51) Int. Cl.
*A61F 2/78* (2006.01)
*A61F 2/76* (2006.01)
*A61F 2/68* (2006.01)
*A61F 2/50* (2006.01)

(52) U.S. Cl.
CPC ............... *A61F 2002/5038* (2013.01); *A61F 2002/6872* (2013.01); *A61F 2002/7856* (2013.01); *A61F 2002/7862* (2013.01)

(56) References Cited

U.S. PATENT DOCUMENTS

| | | | |
|---|---|---|---|
| 2,706,296 A | 4/1955 | Fletcher |
| 2,867,819 A | 1/1959 | George |
| 3,483,718 A | 12/1969 | Lodrini |
| 3,707,963 A | 1/1973 | Keropian |
| 4,258,441 A | 3/1981 | Bell |
| 4,813,406 A | 3/1989 | Ogle, II |
| 4,997,433 A | 3/1991 | Goble et al. |
| 5,062,855 A | 11/1991 | Rincoe |
| 5,941,914 A | 8/1999 | Jacobsen et al. |
| 6,416,703 B1 | 7/2002 | Kristinsson et al. |
| 6,908,489 B2 | 6/2005 | Didrick |
| 8,337,568 B2 | 12/2012 | Macduff |
| 9,375,319 B2 | 6/2016 | Macduff |
| 2004/0054424 A1 | 3/2004 | Matsuda |
| 2005/0043822 A1 | 2/2005 | Didrick |
| 2006/0212129 A1 | 9/2006 | Lake et al. |
| 2006/0224249 A1 | 10/2006 | Winfrey |
| 2008/0127768 A1 | 6/2008 | Shirai et al. |
| 2008/0262636 A1 | 10/2008 | Puchhammer |
| 2010/0042229 A1 | 2/2010 | Hawk |
| 2010/0082103 A1 | 4/2010 | Blunn et al. |
| 2010/0191343 A1 | 7/2010 | Puchammer et al. |
| 2010/0262057 A1 | 10/2010 | Chandrasekhar et al. |
| 2011/0144770 A1 | 6/2011 | Moyer et al. |
| 2011/0208322 A1 | 8/2011 | Rifkin, Jr. et al. |
| 2012/0146352 A1 | 6/2012 | Haslinger |
| 2012/0303136 A1 | 11/2012 | Macduff |
| 2012/0330432 A1 | 12/2012 | Fong |
| 2013/0226315 A1 | 8/2013 | Varley |
| 2013/0268094 A1 | 10/2013 | Van Wiemeersch |
| 2014/0078118 A1 | 3/2014 | Robb |
| 2014/0202741 A1 | 7/2014 | Macduff |
| 2014/0303749 A1 | 10/2014 | Macduff |
| 2014/0303750 A1 | 10/2014 | Macduff |
| 2014/0371897 A1 | 12/2014 | Lin et al. |
| 2015/0138968 A1 | 9/2015 | Hunter |

OTHER PUBLICATIONS

International Search Report and Written Opinion dated Nov. 4, 2016 for Int. Application No. PCT/US2016/048758, 7 pp.
International Search Report and Written Opinion dated Aug. 26, 2016 for Int. Application No. PCT/US2016/032721, 20 pp.
International Search Report and Written Opinion dated Aug. 25, 2016 for Int. Application No. PCT/US2016/032732, 11 pp.
International Search Report and Written Opinion dated Jun. 10, 2016 for Int. Application No. PCT/US2016/016219, 6 pp.
Pop, S., "Finger Prosthetic Shows Perfect Balance Between Flexibility and Sturdiness—Gallery", Oct. 23, 2014, 9 pp.
International Search Report and Written Opinion dated Jun. 2, 2016 for Int. Application No. PCT/US2016/016223, 12 pp.
Leow, M., et al., "Optimal Circumference Reduction of Finger Models for Good Prosthetic Fit of a Thimble-Type Prosthesis for Distal Finger Amputations", Journal of Rehabilitation Research and Development, Mar. 2001, vol. 38, No. 2; pp. 273-279.
Cabibihan, J., "Patient-Specific Prosthetic Fingers by Remote Collaboration—a Case Study", PLoS ONE, May 2011, vol. 6, No. 5.
International Search Report and Written Opinion dated Apr. 22, 2016 for Int. Application No. PCT/US2016/016215, 8 pp.

BIDIRECTIONAL BIOMECHANICAL PROSTHETIC FULL FINGER CONFIGURED FOR ABDUCTION AND ADDUCTION WITH MCP PIVOT

REFERENCE TO PENDING PRIOR PATENT APPLICATIONS

The application claims the benefit under 35 U.S.C. 119 (e) of U.S. Provisional Patent Application No. 62/162,516, filed May 15, 2015 by Jon Bengtsson and Robert Thompson for "BIO-MECHANICAL PROSTHETIC FULL FINGER CONFIGURED FOR ABDUCTION AND ADDUCTION WITH MCP PIVOT," and 62/209,836, filed Aug. 25, 2015 by Robert Thompson JR., Jon Bengtsson, Anthony Charles Peto, Sydney Tye Minnis, Eric Dennis Klumper, and Bradley Arthur Crittenden for "BIO-MECHANICAL PROSTHETIC FULL FINGER CONFIGURED FOR ABDUCTION AND ADDUCTION WITH MCP PIVOT," both of which patent applications are hereby incorporated herein by reference.

BACKGROUND

If a person loses finger mobility, finger functionality, or all or a segment of his or her physical finger, the result is impaired performance of the hand. Having an amputated or minimally functioning finger (e.g., due to nerve damage, excessive scar tissue, neurological damage or disorders, or other bone or musculature dysfunctionalities) inhibits the person from performing some of the most basic tasks. For example, with one or more dysfunctional fingers, the task of typing on a computer keyboard or dialing on a telephone becomes significantly more difficult. These types of tasks require precise actions that only fingers are able to offer.

Not only do fingers allow for the performance of precise physical actions, they also provide an increased ability to grip or handle items. While holding an item in the hand, the weight of the item is dispersed through all of a user's fingers. By varying the force used by each finger on the holder's hand, the holder is able to manipulate the item in a myriad of ways. However, if the holder is missing all or even part of a single finger/digit, or if a finger is present but nonfunctioning, this freedom of manipulation and the number of degrees through which the holder can manipulate the item is drastically decreased.

A primary category of current prosthetic finger solutions is designed to be worn passively and offer a realistic look. These solutions provide little to no functionality and do not enable the owner to restore functionality to his or her hand. Other prosthetics offer the user some level of restored functionality, but are complex in design and either depend on a motorized actuator to articulate the prosthetic or specifically claim to anchor to the user's hand through a "stationary matrix," which may, for instance, include a bracket that slips over the user's residual finger stub. These prosthetics, while perhaps better than going without, are impractical in that they often require an external power source and/or can be limited in functionality and both bulky and unwieldy for the user to manage. Still other prosthetic fingers and/or braces are body-powered but lack the design flexibility necessary to accommodate any length of residual finger while providing maximum dexterity, grip strength, and finger articulation in an attractive, low-profile device.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a prosthetic full finger assembly including (1) a eccentric metacarpophalangeal (MCP) pivot configured for swivelable attachment to a hand of a user; (2) a distal coupler; (3) a proximal rocker rotatively coupled between the MCP pivot at a proximal end thereof and the distal coupler at a distal end thereof; (4) an adjustable ring tendon rotatively coupled to the MCP pivot at a proximal end thereof and the distal coupler at a distal end thereof; (5) a ring disposed upon the adjustable ring tendon, the ring configured to receive and retain a residual finger of the user. The adjustable ring tendon together with the proximal rocker are configured to utilize articulation movements of the residual finger within the ring to articulate the distal coupler within a plane parallel to an x-z plane and about one or more axes parallel to a y axis, and the MCP pivot is configured to utilize abduction and adduction movements of the residual finger within the ring to articulate the distal coupler within a plane parallel to an x-y plane and about an axis parallel to a z axis.

Another embodiment provides a biomechanically driven prosthetic finger. The prosthetic finger includes a hand strap configured to attach about a hand of a user. The prosthetic finger also includes an MCP pivot attached to the hand strap, the MCP pivot having an articulation joint configured to rotate the MCP pivot relative to the hand strap within a plane parallel to an x-y plane and about an axis parallel to a z axis. The prosthetic finger further includes a distal coupler and an articulation assembly pivotally coupled between the MCP joint and the distal coupler, where the articulation assembly is configured to articulate relative to the hand strap within a plane parallel to an x-z plane and about one or more axes parallel to a y axis. The articulation assembly includes (1) a proximal rocker pivotally coupled between the distal coupler and the MCP joint; (2) an adjustable ring tendon pivotally coupled between the distal coupler and the MCP joint, the adjustable ring tendon having a longitudinal adjustment mechanism disposed therein, the longitudinal adjustment mechanism having a proximal end and a distal end; and (3) a ring configured to fit about a residual finger of the user, the ring disposed upon the adjustable ring tendon at a target location between the proximal and distal ends of the longitudinal adjustment mechanism, the target location based on a length of the residual finger.

An additional embodiment provides a method of fitting a biomechanically driven finger assembly having a ring configured to receive a user's residual finger, the ring disposed upon an adjustable ring tendon that is rotatively coupled between a distal coupler and an MCP pivot. The method includes (1) assessing a length of the residual finger; (2) adjusting the ring along a longitudinal adjustment mechanism of the adjustable ring tendon to a target location, the target location based on the length of the residual finger; (3) securing the ring within the longitudinal adjustment mechanism of the adjustable ring tendon at the target location; and (4) sliding the assembly onto the residual finger such that the ring fits about the residual finger at a location that aligns the MCP pivot above an MCP joint of the user.

A further embodiment provides a biomechanical finger assembly for a user's residual finger. The finger assembly includes (1) an eccentric MCP pivot; (2) a distal coupler; (3) an adjustable ring tendon having a distal end and a proximal end in opposition to one another, the distal end pivotally attached to the distal coupler and the proximal end pivotally attached to the MCP pivot, the adjustable ring tendon having a longitudinal adjustment mechanism; (4) a ring configured to concentrically receive and retain the residual finger, the ring disposed upon the adjustable ring tendon at a target location along the longitudinal adjustment mechanism; and (5) a proximal rocker having a distal end and a proximal end in opposition to one another, the distal end of the proximal rocker pivotally attached to the distal coupler and the proximal end of the proximal rocker pivotally attached to the MCP pivot. The adjustable ring tendon together with the proximal rocker are configured to utilize vertical movements of the residual finger within the ring to articulate the distal coupler within a plane parallel to an x-z plane and about one or more axes parallel to a y axis, and the MCP pivot is configured to utilize abduction and adduction movements of the residual finger within the ring to articulate the distal coupler within a plane parallel to an x-y plane and about an axis parallel to a z axis.

Another embodiment provides a bidirectional biomechanically driven finger assembly. The finger assembly includes an MCP pivot having (1) an anchor plate having top and bottom surfaces; (2) a frame having proximal and distal ends and top and bottom surfaces, the bottom surface of the proximal end of the frame disposed upon the top surface of the anchor plate; and (3) an articulation joint, the articulation joint pinning the anchor plate and frame together such that they revolve relative to one another about an axis parallel to a z axis. The finger assembly also includes a distal coupler and an adjustable articulation assembly that rotatively couples the MCP pivot and the distal coupler, the adjustable articulation assembly adjusted to receive a residual finger of a user at a target location that causes the MCP pivot to align with an MCP joint of the user. The adjustable articulation assembly is configured to utilize articulation movements of the residual finger within the adjustable articulation assembly to articulate the distal coupler within a plane parallel to an x-z plane and about one or more axes parallel to a y axis, and the MCP pivot is configured to utilize lateral movements of the residual finger within the adjustable articulation assembly to displace the distal coupler within a plane parallel to an x-y plane and about the axis parallel to the z axis.

Yet another embodiment provides a method of biomechanically operating a bidirectional prosthetic finger assembly including an adjustable articulation assembly rotatively coupled between an MCP pivot and a distal coupler, the adjustable articulation assembly having a ring configured to receive a residual finger of a user's hand. The method includes (1) assessing a length of the residual finger; (2) adjusting the ring to a target location along a longitudinal adjustment mechanism of the adjustable articulation assembly, the target location based on the length of the residual finger; (3) securing the ring within the longitudinal adjustment mechanism at the target location; (4) sliding the prosthetic finger assembly onto the residual finger, such that the ring encircles the residual finger adjacent to the target location and the MCP pivot aligns with an MCP joint of the user; (5) moving the residual finger vertically within the ring, thereby causing the articulation assembly together with the distal coupler to articulate within a plane parallel to an x-z plane in a manner that emulates a finger's natural articulation; and (6) moving the residual finger laterally within the ring, thereby causing the MCP pivot to rotate about an axis parallel to a z axis within a plane parallel to an x-y plane, such that the articulation assembly together with the distal coupler abduct away from a midline of the hand and adduct toward the midline of the hand.

An additional embodiment provides a bidirectional biomechanical finger assembly for a user's residual finger having an MCP pivot, a distal coupler, and an articulation assembly rotatively coupled between the MCP pivot and the distal coupler. The articulation assembly includes (1) an adjustable ring tendon having a distal end, a proximal end, and a longitudinal adjustment mechanism disposed therebetween, the proximal end rotatively coupled with the MCP pivot; (2) a ring configured to receive and retain the residual finger, the ring selectively disposed upon the adjustable ring tendon at a target location along the longitudinal adjustment mechanism; (3) a proximal coupler; and (4) a distal rocker. The proximal coupler and the distal rocker are rotatively suspended between a proximal coordinated pivot point anchored upon the adjustable ring tendon and a distal coordinated pivot point anchored upon the distal coupler.

Another embodiment provides a bidirectional biomechanically driven prosthetic finger. The prosthetic finger includes an MCP pivot for attachment to a hand of a user, the MCP pivot having an articulation joint configured to rotate the MCP pivot relative to the hand within a plane parallel to an x-y plane and about an axis parallel to a z axis. The prosthetic finger also includes a distal coupler and an articulation assembly hingedly coupled between the MCP joint and the distal coupler, the articulation assembly configured to articulate relative to the hand within a plane parallel to an x-z plane and about one or more axes parallel to a y axis. The articulation assembly includes a proximal coupler rotatively coupled with the distal coupler via a first hinged connection and an adjustable ring tendon having a proximal end, a distal end, and a ring disposed thereon, where (1) the ring is configured to anchor onto a residual finger of the user; (2) the ring is slidably adjustable between the proximal and distal ends of the adjustable ring tendon; (3) the adjustable ring tendon is rotatively coupled with the proximal coupler via a third hinged connection; and (4) the first and third hinged connections define a midline relative to the z axis. The articulation assembly also includes a distal rocker extending between the distal coupler and the adjustable ring tendon, the distal rocker having a distal end and a proximal end, the distal end of the distal rocker rotatively coupling with the distal coupler via a second hinged connection located below the midline, the proximal end of the distal rocker rotatively coupling with the adjustable ring tendon via a fourth hinged connection located above the midline.

Yet another embodiment includes a method of biomechanically operating a bidirectional prosthetic finger assembly having a hand strap, an MCP pivot affixed to the hand strap, a distal coupler, and an adjustable articulation assembly rotatively coupled between the MCP pivot and the distal coupler, the adjustable articulation assembly including a ring configured to receive a residual finger of a user's hand. The method includes (1) assessing a length of the residual finger; (2) adjusting the ring to a target location along the adjustable articulation assembly, the target location based on the length of the residual finger; (3) securing the ring at the target location; (4) sliding the prosthetic finger assembly onto the residual finger such that the ring encircles the residual finger adjacent to the target location and the MCP pivot aligns with an MCP joint of the user; and (5) securing the hand strap about the hand.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments disclosed herein relate to a custom-designed, self-contained, bidirectional, biomechanically driven prosthetic finger assembly that can be fitted for a user with an amputated fingertip or finger segment. The streamlined and sophisticated design allows for a patient with any level of residual finger to utilize a mechanical prosthetic finger that mimics both the vertical and lateral motions and functionalities of a real finger. The natural movement of the prosthetic finger assembly allows users to regain maximum control of the flexion, extension, abduction, and adduction movements of a fully functioning finger and fingertip and is designed to articulate in a realistic, natural manner in response to movement in the user's own residual finger and/or adjacent fingers.

Embodiments described herein include a ring that is configured to receive and retain a user's residual finger and/or adjacent fingers along with an adjustable ring tendon, both discussed in detail below. The ring and adjustable ring tendon allow the biomechanical prosthetic finger to anchor to any length of residual finger, including an amputation of a fingertip or one or more finger segments, while providing the individual user with maximum fit and use flexibility, dexterity, grip strength, and bidirectional articulation. As a result, the prosthetic finger offers patients experiencing loss of finger/digit function, as well as partial finger amputees, a functional solution that eases the transition back into daily activities, no matter how intricate.

To facilitate explanation of the movement of the bidirectional prosthetic finger discussed herein, relative vertical and lateral movements of the components of the prosthetic finger embodiments discussed below are explained in relation to three axes—an x axis, a y axis, and a z axis—initially defined in FIG. 1. These three axis inherently define two relevant planes of movement—an x-y plane and an x-z plane.

Figure 1:
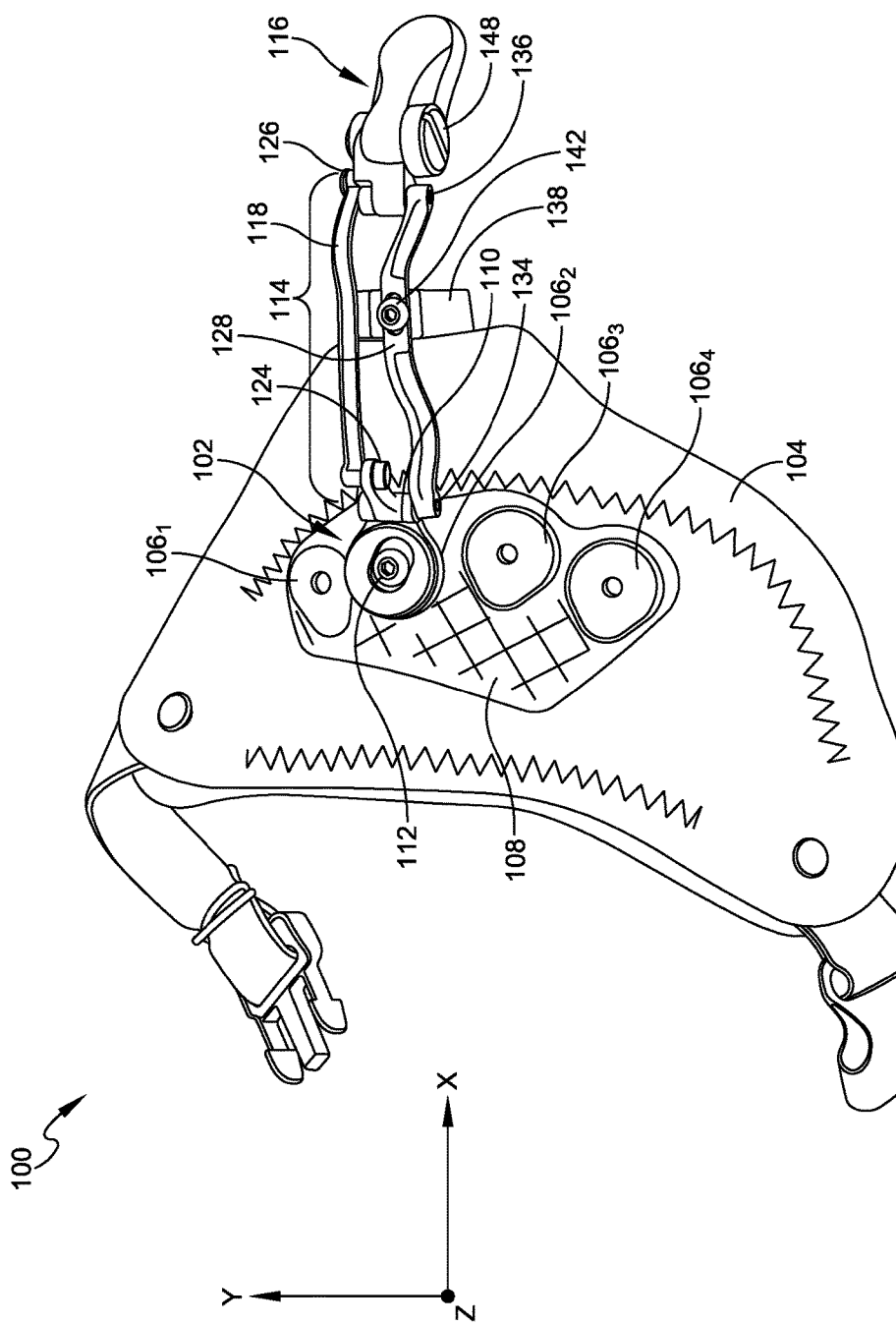
FIG. 1 illustrates a perspective view of one embodiment of a bidirectional biomechanically driven prosthetic finger, as pivotally coupled with a hand strap.
Figure 2:
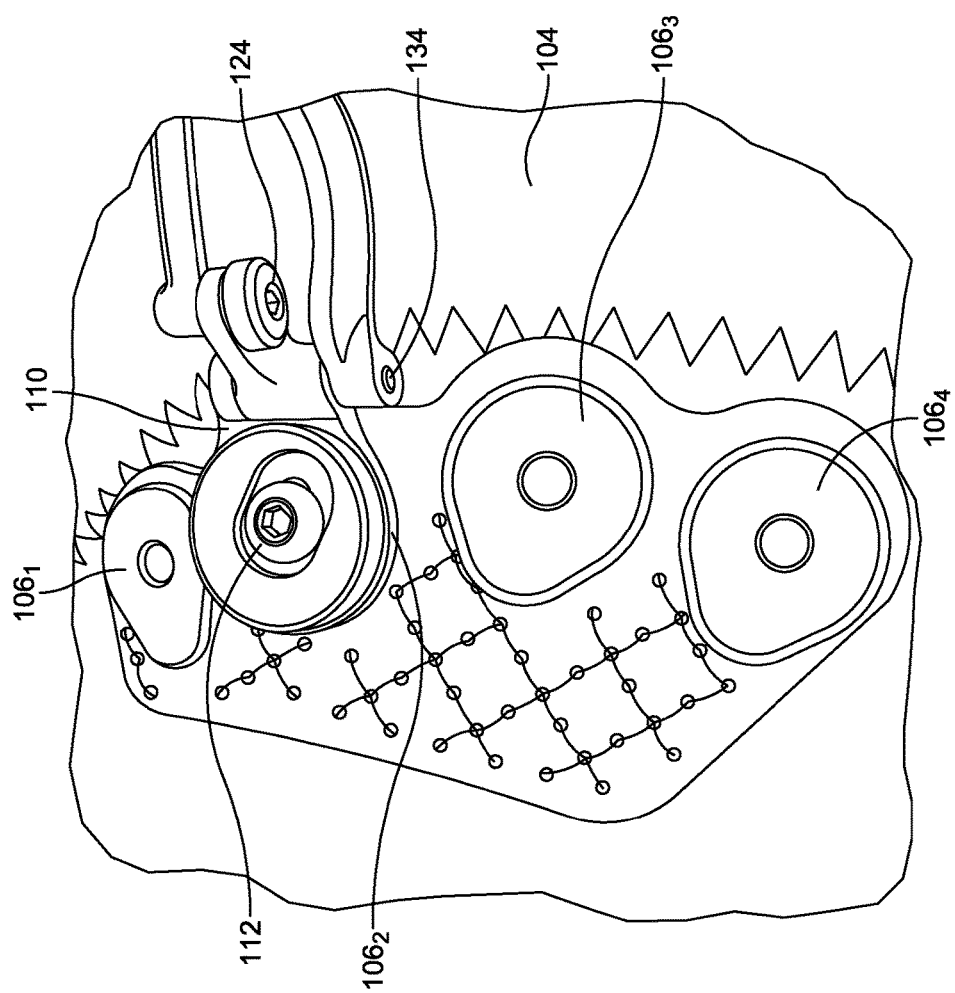
FIG. 2 illustrates a perspective view of a metacarpophalangeal (MCP) pivot of the prosthetic finger of FIG. 1.

Turing to the exemplary embodiments detailed in the figures, FIG. 1 illustrates a perspective view of one embodiment of a bidirectional and biomechanically driven prosthetic finger 100. In this embodiment, prosthetic finger 100 may include an eccentric metacarpophalangeal (MCP) pivot 102 configured to attach to a user's hand via a hand strap 104 adapted to attach about a back of a user's hand (not shown). MCP pivot 102 may include an anchor plate $106_2$, selected from a number of anchor plates $106_{1-4}$ that each align with a different MCP joint and corresponding finger of the user, as shown in further detail in FIG. 2. In one embodiment, anchor plates $106_{1-4}$ may be mounted directly upon hand strap 104, or they may be incorporated within or mounted upon a strap platform 108 to provide an appropriate alignment and/or depth with the rest of prosthetic finger 100.

MCP pivot 102 may also include a frame 110. At its proximal end, frame 110 may be rotationally coupled with anchor plate $106_2$ via an articulation joint 112. Articulation joint 112 may be a pin, a screw, or any other appropriate fastener that joins anchor plate $106_2$ and frame 110 such that frame 110 revolves relative to anchor plate $106_2$ about an axis parallel to the z axis. At its distal end, frame 110 may be rotationally or hingedly coupled with an articulation assembly 114 (FIG. 1).

Figure 3:
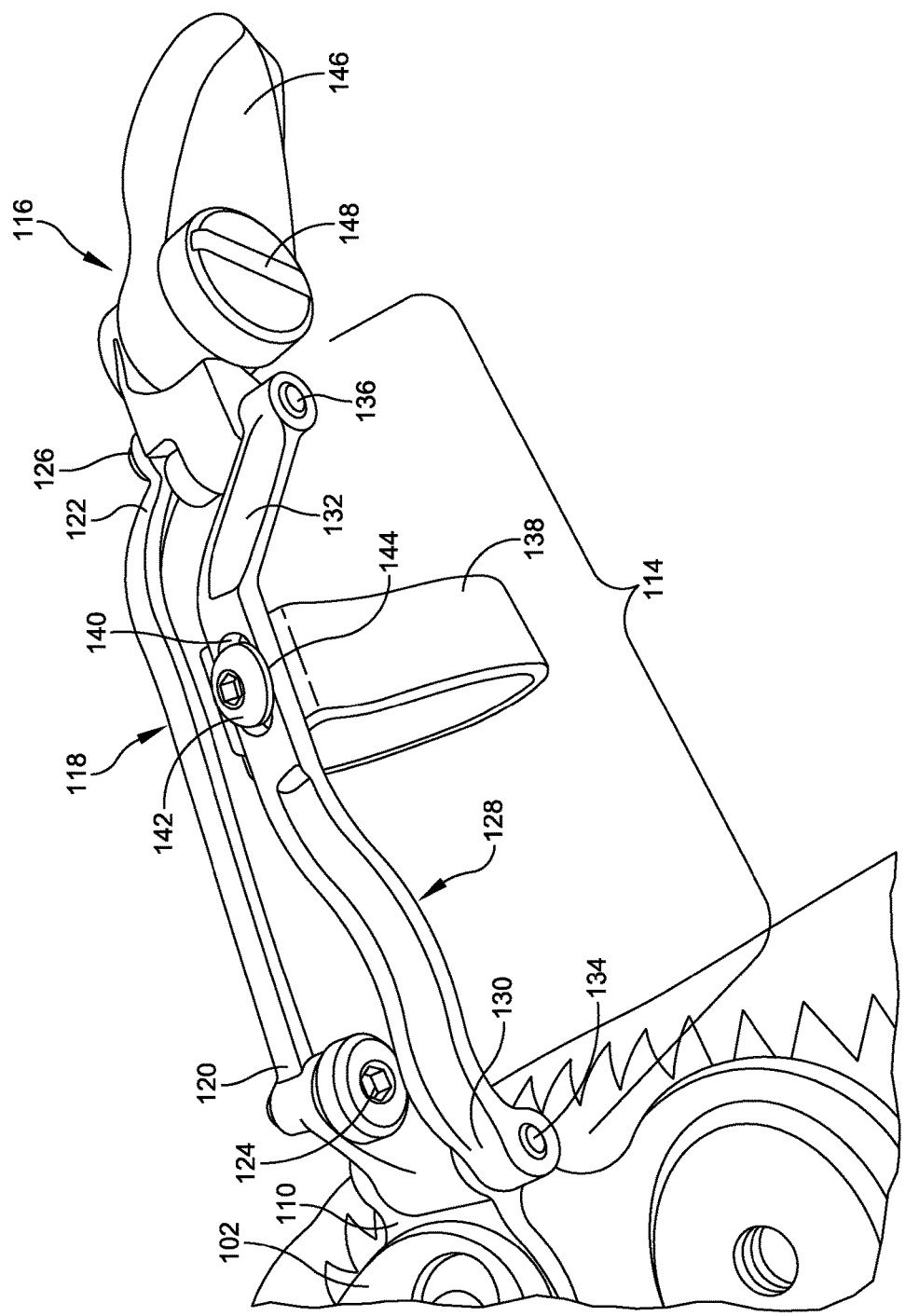
FIG. 3 illustrates a perspective view of an articulation assembly of the prosthetic finger of FIG. 1, as coupled between the MCP pivot of FIG. 2 and a distal coupler.

FIG. 3 illustrates a perspective view of articulation assembly 114, as rotatively coupled between eccentric MCP joint 102 and a distal coupler 116. In this embodiment, articulation assembly 114 may include a proximal rocker 118 having a proximal end 120 and a distal end 122 thereof. Proximal end 120 of proximal rocker 118 may rotatively couple with frame 110 via a hinged connection 124, and distal end 122 of proximal rocker 118 may rotatively couple with distal coupler 116 via a hinged connection 126.

Articulation assembly 114 may also include an adjustable ring tendon 128. Adjustable ring tendon 128 may have a proximal end 130 and a distal end 132. In this embodiment, proximal end 130 of adjustable ring tendon 128 may rotatively couple with frame 110 via a hinged connection 134. Distal end 132 of adjustable ring tendon 128 may rotatively couple with distal coupler 116 via a hinged connection 136.

In one embodiment, a ring 138 may be disposed upon adjustable ring tendon 128. Ring 138 may be configured to concentrically receive and retain the user's residual finger and may be formed of any appropriate metal and/or plastic material. Ring 138 may incorporate a silicone portion or portions for improved grip, comfort, and serviceability. These silicone portions may reside along a lower portion of ring 128 and/or they may be incorporated along natural pressure points between the finger and ring 128, such as at the top of the proximal phalanx bone.

Ring 138 may be adjusted along the length of adjustable ring tendon 128 by sliding ring 138 along a longitudinal adjustment mechanism disposed within tendon 128. In this embodiment, the longitudinal adjustment mechanism may be a longitudinal adjustment channel 140 formed within tendon 128. To adjust ring 138, a user may simply slide ring 138 along a length of channel 140 before securing ring, via a screw 142 or any other appropriate fastener, to tendon 128 at a target location 144 along channel 140. Target location 144 may be based on a length of the user's residual finger and result in an alignment of MCP pivot 102 above/over the user's MCP joint when the user's finger is retained within ring 138. Longitudinal adjustment channel 140 may have any appropriate length along adjustable ring tendon 128. Further, the longitudinal adjustment mechanism may take any appropriate size, shape, type, and/or configuration. For example, in an alternate embodiment, the longitudinal adjustment mechanism may be formed from a number of longitudinal adjustment holes disposed along the length of longitudinal adjustment tendon 128.

Figure 4:
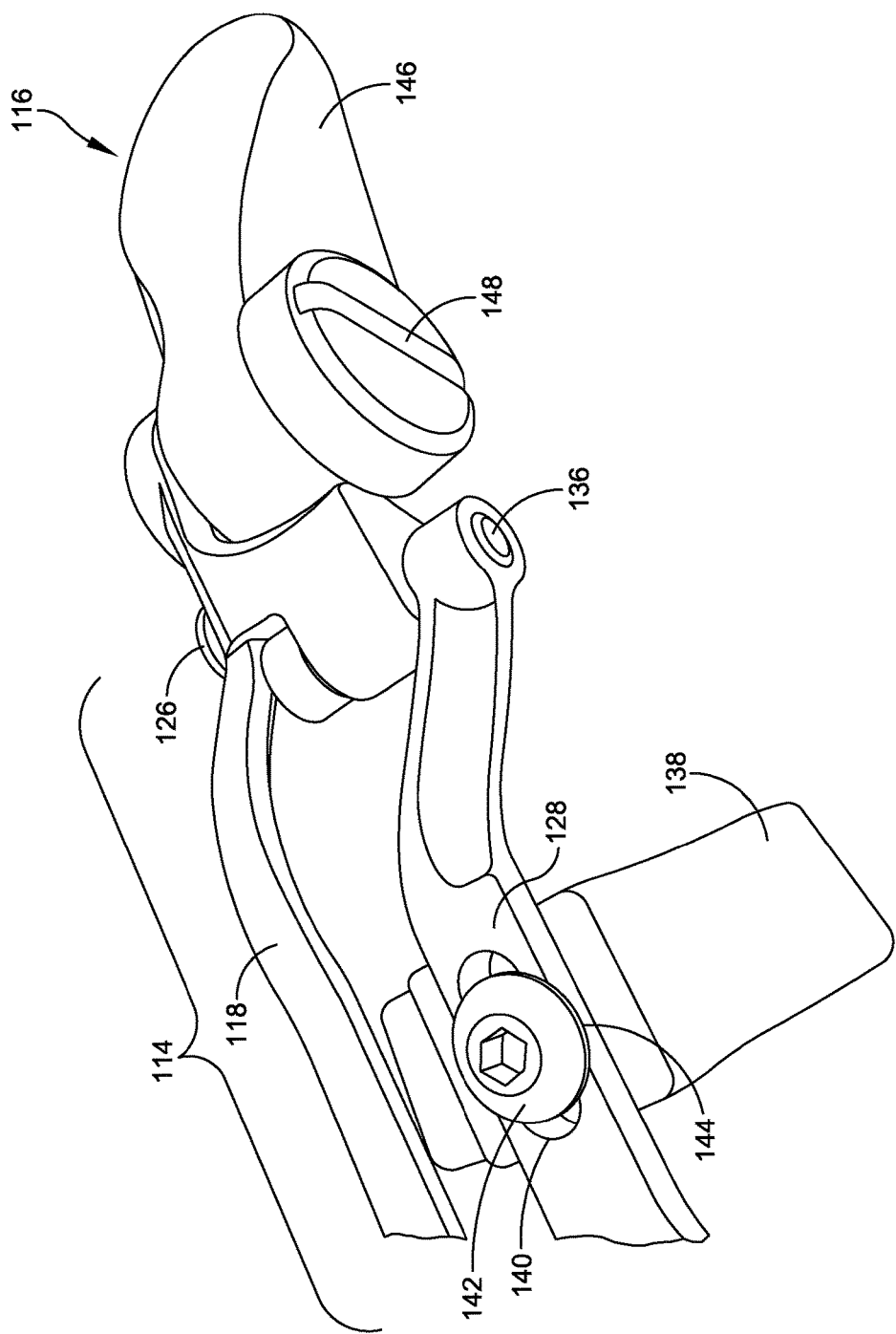
FIG. 4 illustrates a perspective view of the distal coupler of FIG. 3.

FIG. 4 illustrates a perspective view of distal coupler 116, as rotatively coupled with a proximal end of articulation assembly 114. As discussed above, distal coupler 116 may rotatively couple with articulation assembly 114 via hinged connections 126 and 136. Distal coupler 116 may include a tip pad 146. Tip pad 146 may be formed from a soft-textured silicone or other material that mimics the texture of a real finger. This aids with gripping and provides a softer touch. In one embodiment, a touchscreen mechanism (not shown) may be provided to allow the user to use prosthetic finger 100 to operate capacitive touchscreens, which react to the body's natural current. The touchscreen mechanism allows the user to direct his or her own body current through distal coupler 116.

In this embodiment, distal coupler 116 may include a distal interphalangeal (DIP) adjustment connector 148. DIP adjustment connector 148 may be a screw or another appropriate fastener that allows distal coupler 116 to be adjusted through 360 degrees of rotation, limited only by interference with other components of prosthetic finger 100. DIP adjustment connector 148 may be tightened at any desired angle, lending distal coupler 116 infinite adjustment options within a full range of feasible and/or desirable fingertip angles.

As discussed above and returning to FIG. 1, articulation assembly 114 and distal coupler 116 are designed for bidirectional articulation. Specifically, assembly 114 and distal coupler 116 may rotate laterally relative to MCP pivot 102 via articulation joint 112, providing prosthetic finger 100 with a first direction of movement about an axis parallel to the z axis and within a plane parallel to the x-y plane. Hinged connections 124 and 134, which rotatively couple articulation assembly 114 to MCP pivot 102, as well as hinged connections 126 and 136, which rotatively couple articulation assembly 114 with distal coupler 116, provide a second, vertical direction of movement about axes parallel to the y axis and within planes parallel to the x-z plane. As a result, the user may achieve more lifelike movements of distal coupler 116 that emulate the natural articulation of a finger by moving his or her residual finger laterally (e.g., adducting and/or abducting the residual finger) within ring 138 to actuate finger 100 in the first direction, and by moving his or her residual finger vertically within ring 138 to actuate finger 100 in the second direction, thereby achieving both lateral and vertical articulation of distal coupler 116.

Figure 5:
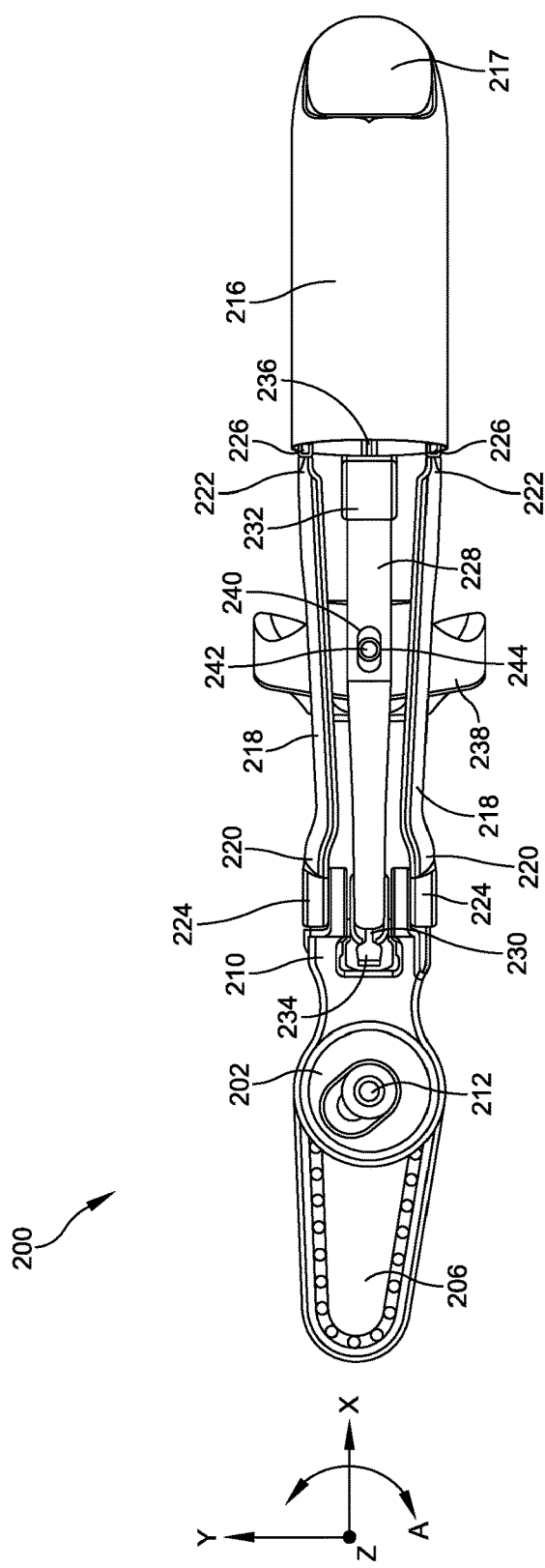
FIG. 5 illustrates a top view of another embodiment of a bidirectional biomechanically driven prosthetic finger.
Figure 6:
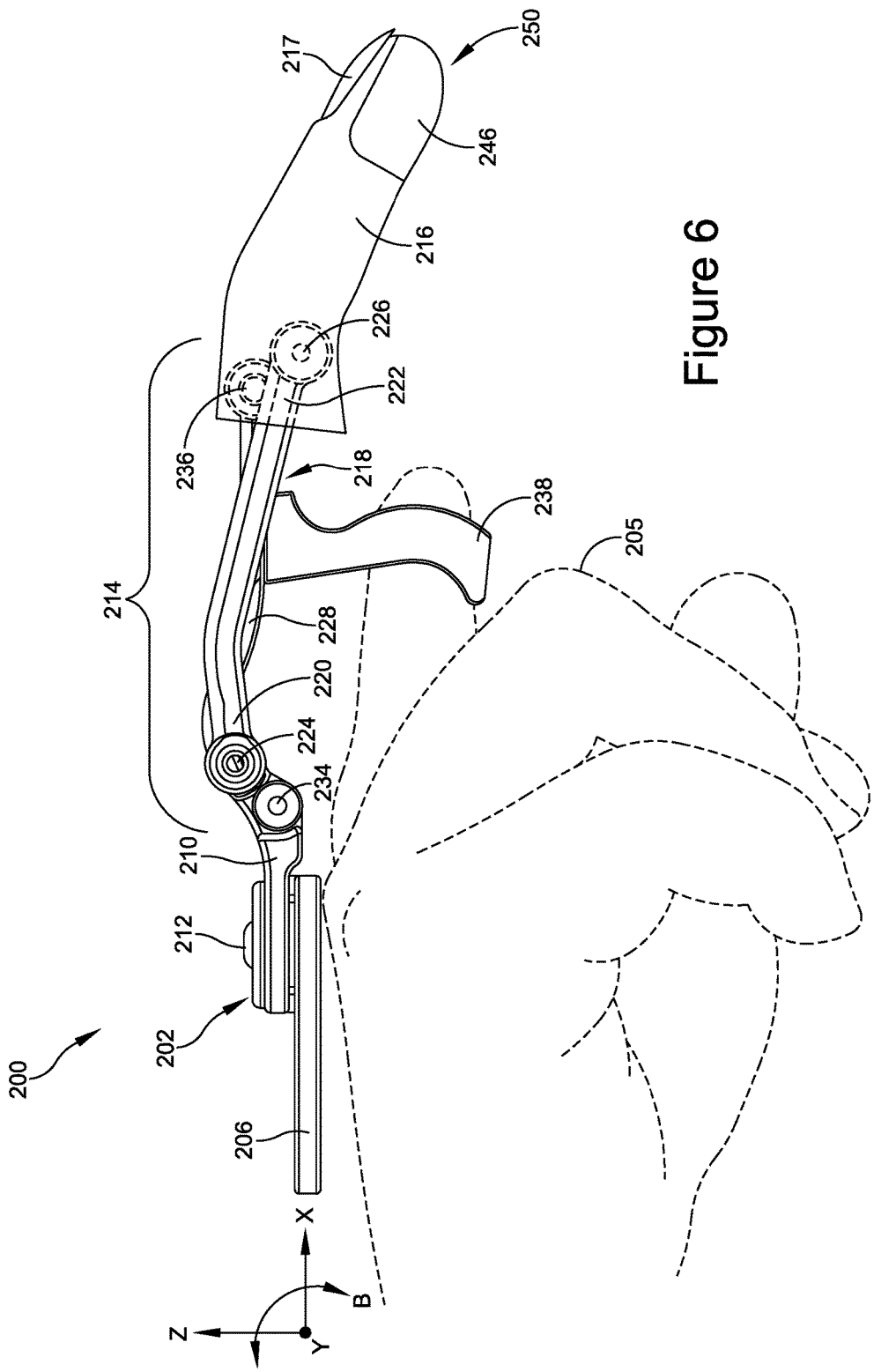
FIG. 6 illustrates a side view of the prosthetic finger of FIG. 5, disposed above a hand of a user and in an extended position.
Figure 7:
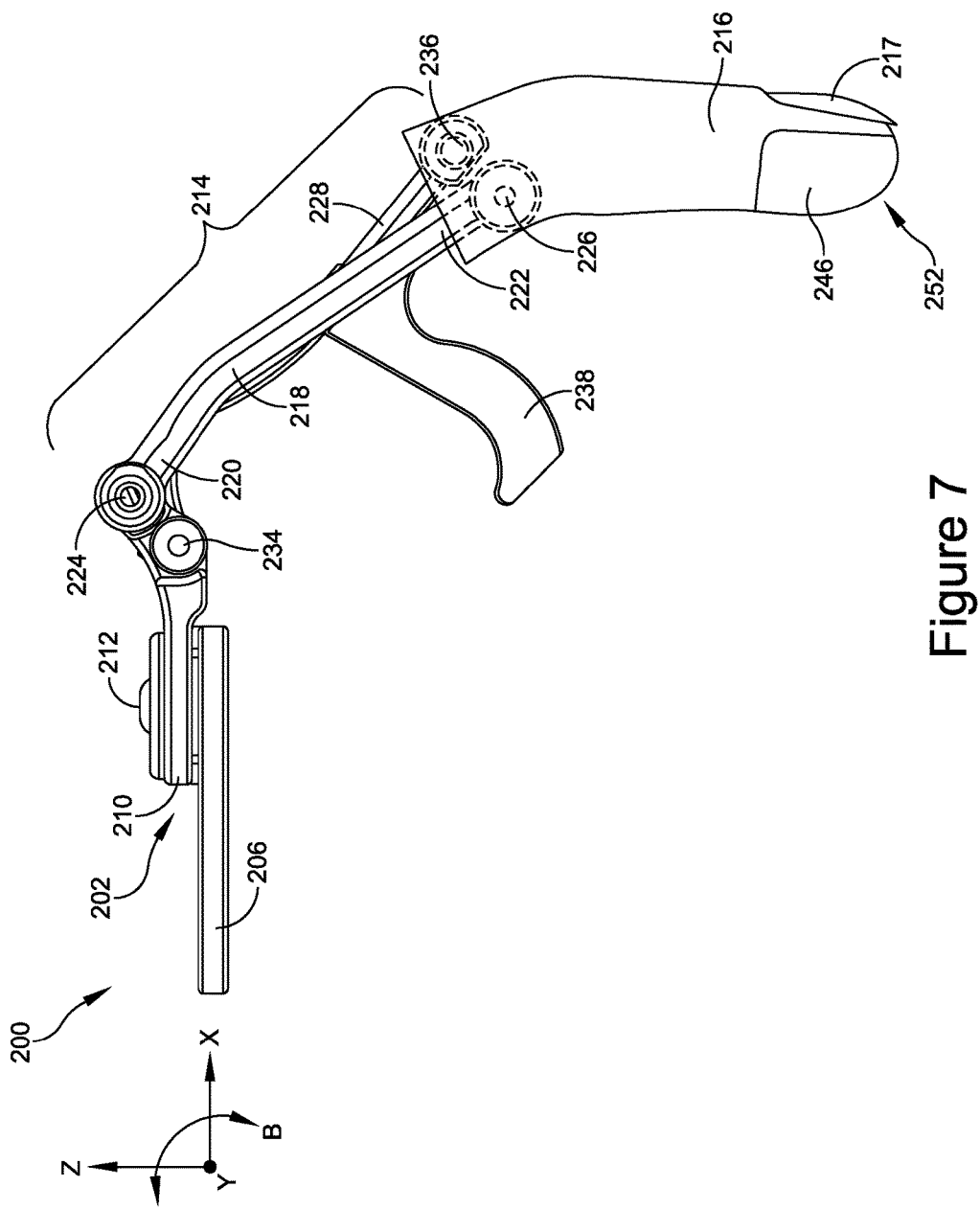
FIG. 7 illustrates a side view of the prosthetic finger of FIG. 5 in a retracted or curled position.

FIGS. 5-7 illustrate respective top, side-extended, and side-curled (i.e., retracted) views of another exemplary embodiment of a bidirectional and biomechanically driven prosthetic finger 200. In one embodiment, prosthetic finger 200 may include an eccentric MCP pivot 202 configured to attach to a user's hand via a hand strap (not shown) adapted to attach about a back of a user's hand. MCP pivot 202 may include an anchor plate 206 designed to align with a select/corresponding residual finger of the user. In one embodiment, anchor plate 206 may be mounted directly upon the hand strap via any reasonable and/or appropriate means (e.g., sewn, riveted, adhered, etc.). In another embodiment, the hand strap and anchor plate 206 may be molded or otherwise manufactured as a single piece.

MCP pivot 202 may also include a frame 210. At its proximal end, frame 210 may be rotationally coupled with anchor plate 206 via an articulation joint 212 adapted for positioning above the user's MCP joint. Articulation joint 212 may be a pin, a screw, or any other appropriate fastener that joins anchor plate 206 and frame 210 such that frame 210 revolves relative to anchor plate 206 about an axis parallel to the z axis. At its distal end, frame 210 may be rotationally or hingedly coupled with an articulation assembly 214 that is rotatively coupled between MCP joint 202 and a distal coupler 216.

In further detail and in this embodiment, articulation assembly 214 may include a two-piece, mirror-image proximal rocker 218 having a proximal end 220 and a distal end 222. Proximal end 220 of proximal rocker 218 may rotatively couple with frame 210 via a hinged connection formed of two mirror-image hinged connections 224. Distal end 222 of proximal rocker 218 may rotatively couple with distal coupler 216 via a hinged connection formed of two mirror-image hinged connections 226.

Articulation assembly 214 may also include an adjustable ring tendon 228. Adjustable ring tendon 228 may have a proximal end 230 and a distal end 232. In this embodiment, proximal end 230 of adjustable ring tendon 228 may rotatively couple with frame 210 via a hinged connection 234. Distal end 232 of adjustable ring tendon 228 may rotatively couple with distal coupler 216 via a hinged connection 236.

In one embodiment, a ring 238 may be disposed upon adjustable ring tendon 228. Ring 238 may be configured to receive and retain the user's residual finger and may be formed of any appropriate metal and/or plastic material. As discussed above in relation to ring 138, ring 238 may incorporate a silicone portion or portions for improved grip, comfort, and serviceability. These silicone portions may reside along a lower portion of ring 238 and/or they may be incorporated along natural pressure points between the finger and ring 238, such as at the top of the proximal phalanx bone.

Ring 238 may be adjusted along the length of adjustable ring tendon 228 by sliding ring 238 along a longitudinal adjustment mechanism formed within tendon 228. In this embodiment, the longitudinal adjustment mechanism may be a longitudinal adjustment channel 240 formed within tendon 228. To adjust, a user may slide ring 238 along a length of channel 240 before securing ring 238, via a screw 242 or any other appropriate fastener, to tendon 228 at a target location 244 along channel 240. Target location 244 may be based on a length of the user's residual finger and result in an alignment of MCP pivot 202 above/over the user's MCP joint when the user's finger is retained within ring 238, as shown in FIG. 6. Longitudinal adjustment channel 240 may have any appropriate length. The longitudinal adjustment mechanism may take any appropriate size, shape, type, and/or configuration. For example, in other embodiments, the longitudinal adjustment mechanism may be a number of longitudinal adjustment holes disposed along the length of longitudinal adjustment tendon 228 or may be a retention ridge incorporated into tendon 228 and designed to engage with a clamp or other securement device incorporated into ring 238.

As discussed above, distal coupler 216 may rotatively couple to articulation assembly 214 via hinged connections 226 and 236. Distal coupler 216 may include a tip pad 246. Tip pad 246 may be formed from a soft-textured silicone or other material that mimics the texture of a real finger and with gripping and provides a softer touch. One embodiment of distal coupler 216 may also include a nail 217, which mimics a natural edged fingernail that may provide scratching and peeling functionalities as well as assist with fine-object manipulation.

Like articulation assembly 114 of prosthetic finger 100, articulation assembly 214 and distal coupler 216 of prosthetic finger 200 are designed for bidirectional articulation. Specifically, articulation assembly 214 and distal coupler 216 may rotate laterally relative to the hand via articulation joint 212 of MCP pivot 202, providing prosthetic finger 200 with a first direction of movement about an axis parallel to the z axis and within a plane parallel to the x-y plane. This lateral movement is denoted by arrow A, shown in FIG. 5.

A second, vertical direction of movement is denoted by arrow B, shown in FIGS. 6 and 7. FIG. 6 depicts prosthetic finger 200, as disposed above a hand 205 of a user, in an extended position 250. FIG. 7 depicts the prosthetic finger 200 in a retracted or curled position 252. Specifically, hinged connections 224 and 234, which rotatively couple articulation assembly 214 with frame 210 of MCP pivot 202, as well as hinged connections 226 and 236, which rotatively couple articulation assembly 214 with distal coupler 216, provide multiple rotational connections for movement about numerous axes parallel to the y axis and within planes parallel to the x-z plane. As a result, the user may achieve more lifelike movements of distal coupler 216 that emulate the natural articulation of a finger by moving his or her residual finger laterally (e.g., adducting and/or abducting the residual finger) within ring 238, and/or by moving his or her residual finger vertically within ring 238 to achieve both lateral movement in the direction of arrow A and vertical movement in the direction of arrow B of distal coupler 216.

Figure 8:
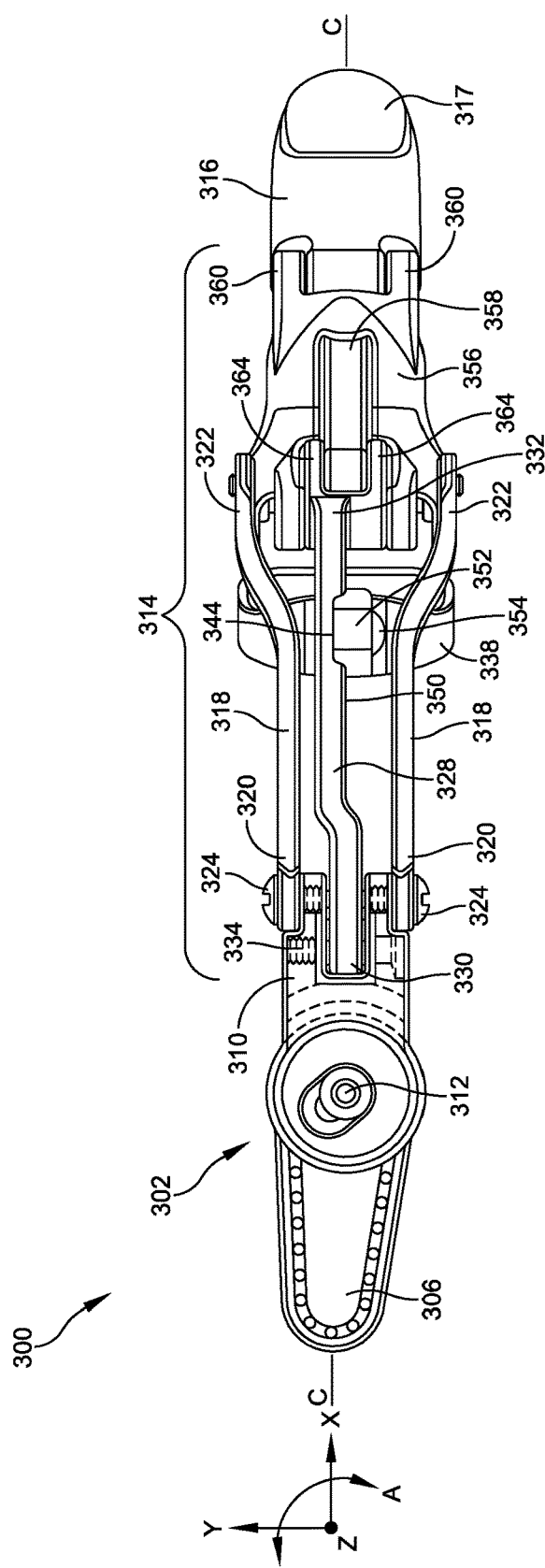
FIG. 8 illustrates a top view of another embodiment of a bidirectional biomechanically driven prosthetic finger.
Figure 9:
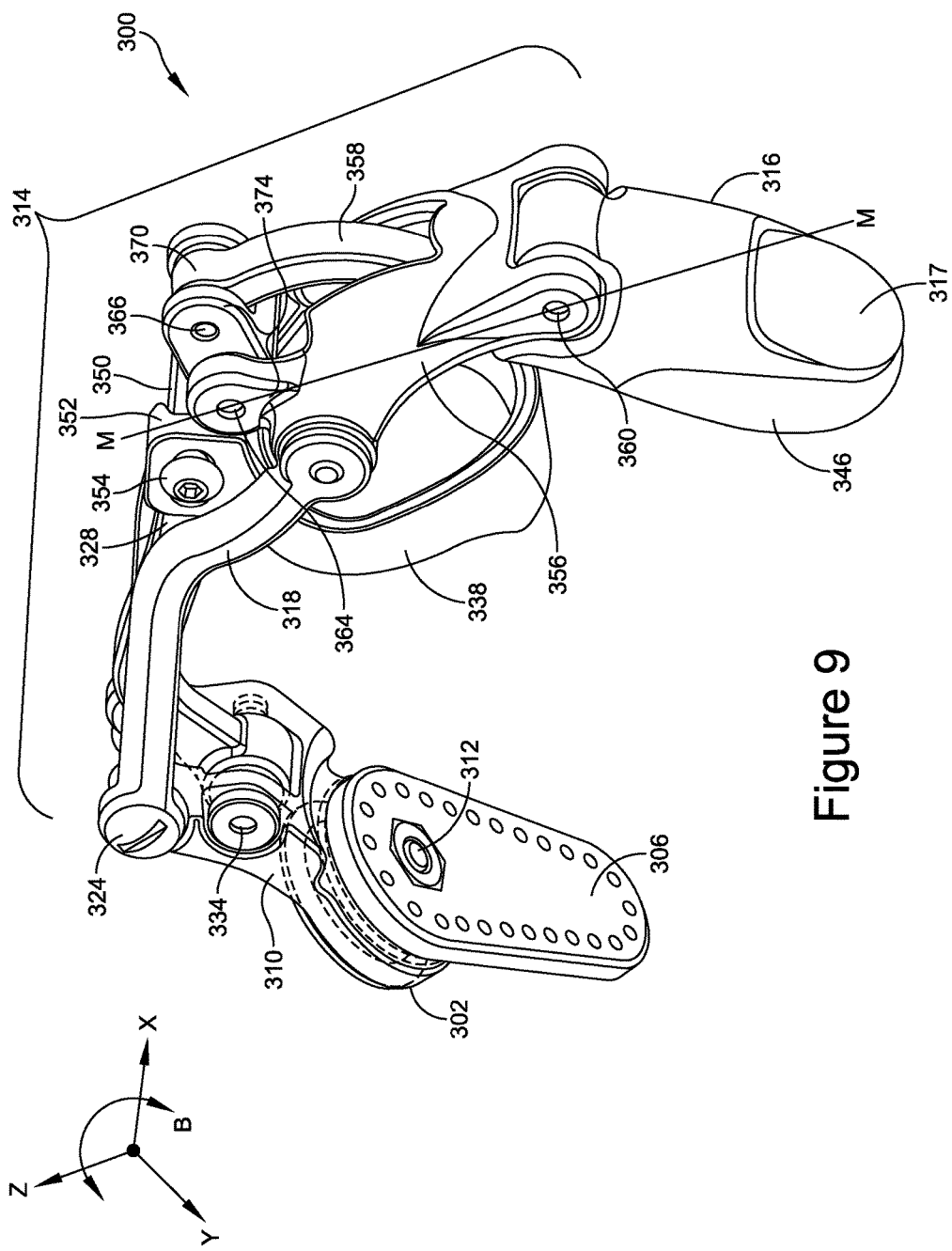
FIG. 9 illustrates a front perspective view of the prosthetic finger of FIG. 8 in a curled position.
Figure 10:
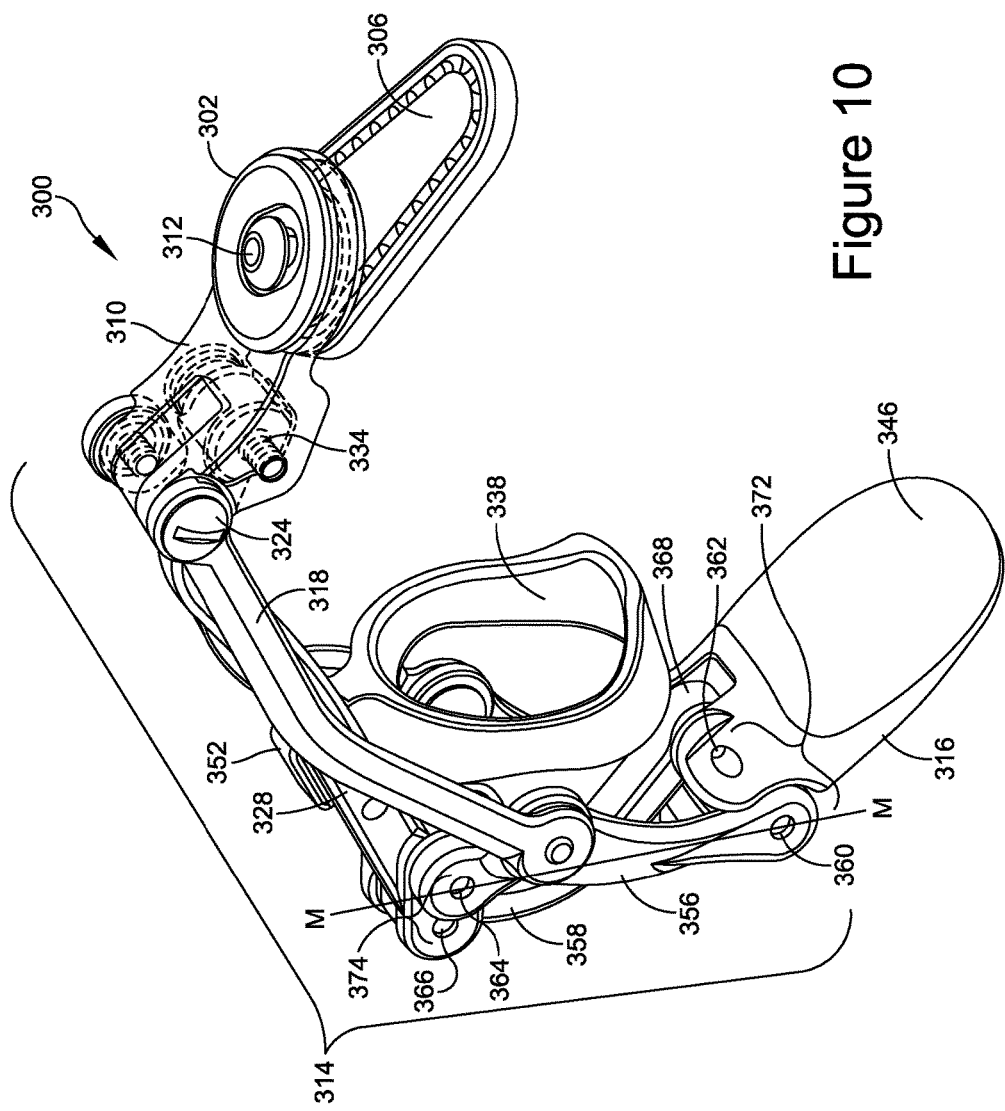
FIG. 10 illustrates a rear perspective view of the prosthetic finger of FIG. 8 in a curled position.

FIGS. 8-10 illustrate respective top, front-perspective, and rear-perspective views of another exemplary embodiment of a bidirectional and biomechanically driven prosthetic finger 300. In one embodiment, prosthetic finger 300 may include an eccentric MCP pivot 302 configured to attach to a user's hand via a hand strap (not shown) adapted to attach about a back of a user's hand or via any other appropriate attachment mechanism. MCP pivot 302 may include an anchor plate 306 designed to align with a corresponding residual finger of the user. In one embodiment, anchor plate 306 may be mounted directly upon the hand strap via any reasonable and/or appropriate means (e.g., sewn, riveted, adhered etc.). In another embodiment, the hand strap and anchor plate 306 may be molded or otherwise manufactured as a single piece.

MCP pivot 302 may also include a frame 310. At its proximal end, frame 310 may be rotationally coupled with anchor plate 306 via an articulation joint 312 adapted for positioning above/over a select one of the user's MCP joints. Articulation joint 312 may be a pin, a screw, or any other appropriate fastener that joins anchor plate 306 and frame 310 such that frame 310 revolves relative to anchor plate 306 about an axis parallel to the z axis. At its distal end, frame 310 may be rotationally or hingedly coupled with an articulation assembly 314 that is rotatively coupled between MCP joint 302 and a distal coupler 316.

In this embodiment, articulation assembly 314 may include a two-piece, mirror-image proximal rocker 318. Proximal rocker 318 may include a proximal end 320 and a distal end 322. Proximal end 320 may rotatively couple with frame 310 via a hinged connection formed of two mirror-image hinged connections 324.

Articulation assembly 314 may also include an adjustable ring tendon 328. Adjustable ring tendon 328 may have a proximal end 330 and a distal end 332. In this embodiment, proximal end 330 of adjustable ring tendon 328 may rotatively couple with frame 310 via a hinged connection 334.

In one embodiment, a ring 238 may be disposed upon adjustable ring tendon 328. Ring 338 may be configured to concentrically receive and retain the user's residual finger and may be formed of any appropriate metal and/or plastic material. As discussed above in relation to rings 138 and 238, ring 338 may incorporate a silicone portion or portions for improved grip, comfort, and serviceability. These silicone portions may reside along a lower portion of ring 338 and/or they may be incorporated along natural pressure points between the finger and ring 338, such as at the top of the proximal phalanx bone.

Ring 338 may be adjusted along the length of adjustable ring tendon 328 by sliding ring 338 along a longitudinal adjustment mechanism of tendon 328. In this embodiment, the longitudinal adjustment mechanism may include a retention ridge 350 designed to engage with a corresponding clamp portion 352 of ring 338. A positioning screw 354 may intersect clamp portion 352 in a manner that allows positioning screw 354, and thus ring 338, to be tightened against adjustable ring tendon 328 at a target location 344 along a length of adjustable ring tendon 328. To adjust, a user may slide ring 338 along the length of adjustable ring tendon 328 before securing ring 338, via positioning screw 354 or any other appropriate fastener, to tendon 328 at target location 344. Target location 344 may be based on a length of the user's residual finger and result in an alignment of MCP pivot 302 above/over the user's MCP joint when the user's finger is retained within ring 338. In other embodiments, the longitudinal adjustment mechanism of adjustable ring tendon 328 may be a longitudinal adjustment channel formed within tendon 328, and to which ring 338 is secured, or a number of longitudinal adjustment holes disposed along the length of longitudinal adjustment tendon 328.

In this embodiment of finger assembly 300, articulation assembly 314 may include a four-bar linkage system that connects with distal coupler 316. In further detail, the four-bar linkage system may include four major interconnected components that extend from distal end 332 of adjustable ring tendon 328 to distal coupler 316. That is, a series of hinges may be used to secure the primary components of the linkage system in a manner that pivotally suspends a proximal coupler 356 and a distal rocker 358 between distal coupler 316 and adjustable ring tendon 328. Proximal rocker 318 may also by hingedly coupled proximal coupler 356 at its distal end 322.

In one embodiment, the hinges of the four-bar linkage may be particularly positioned with respect to a pair of axes detailed in FIGS. 8-10. More specifically, FIG. 8 depicts a centerline, C, that bisects finger assembly 300 relative to they axis, and FIGS. 9-10 show a midline, M, that intersects a first hinged connection 360 and a third hinged connection 364, both detailed below, relative to the z axis when finger 300 is in an extended position.

Turning to the various rotative connections that form the linkage system, proximal coupler 356 may rotatively couple with distal coupler 316 via first hinged connection 360, which may include a pair of parallel pivotal hinges that are symmetric about centerline, C, discussed above in relation to FIG. 8. Each of the pivotal hinges of hinged connection 360 may provide a pivot point between proximal coupler 356 and distal coupler 316 about an axis parallel to the y axis.

At its proximal end, proximal coupler 356 may rotatively couple with adjustable ring tendon 328 via third hinged connection 364. Third hinged connection 364 may also include a pair of parallel pivotal hinges that are symmetric about the centerline, C, one located on each side of assembly 300 such that each provides a pivot point between adjustable ring tendon 328 and proximal coupler 356. As discussed above in relation to FIG. 9, the midline, M, intersects hinged connections 360 and 364, and, therefore both first and third hinged connections 360, 364 are located directly upon the midline, M, relative to the z axis.

Distal rocker 358 may have opposing distal and proximal ends 368, 370, respectively, that extend between distal coupler 316 and adjustable ring tendon 328. Distal end 368 may rotatively couple with distal coupler 316 via a second hinged connection 362 (FIG. 10) located below the midline, M, relative to the z axis. Proximal end 370 may rotatively couple with adjustable ring tendon 328 via a fourth hinged connection 366 located above the midline, M, relative to the z axis. Both second and fourth hinged connections 362 and 366 may include a pair of parallel pivotal hinges that are symmetric about the centerline, C, each providing a respective pivot point between distal rocker 358 and distal coupler 316/adjustable ring tendon 328.

To achieve the "suspension" concept discussed above with respect to proximal coupler 356 and distal rocker 358, first and second hinged connections 360, 362 may align to form a distal coordinated pivot point 372 (FIG. 10), which is anchored upon distal coupler 316. Similarly, third and fourth hinged connections 364, 366 may align to form a proximal coordinated pivot point 374 (FIGS. 9-10). While distal rocker 358 and proximal coupler 356 do not directly connect with one another, they each directly and pivotally connect with distal coupler 316 and adjustable ring tendon 328 via the distal and proximal coordinated pivot points 372, 374, respectively. As a result, distal rocker 358 and proximal coupler 356 are each independently, pivotally suspended between distal coupler 316 and adjustable ring tendon 328, such that they articulate in coordinated, yet independent, manners relative to one another and about numerous axes parallel to the y axis. This association of distal rocker 358 and proximal coupler 356, without an actual direct link or connection between the two components, allows for complex, realistic vertical articulation motions (e.g., motions within planes parallel to the x-z plane) of distal rocker 358, proximal coupler 356, and distal coupler 316 in response to biomechanical input forces exerted on adjustable ring tendon 328 by the residual finger retained therein.

Embodiments of any one or more of the first, second, third, and/or fourth hinged connections 360, 362, 364, 366 may be outfitted with hard-stops to prevent hyperextension of finger 300 during operation. Mechanical hard-stops may have any appropriate size, shape, and/or configuration.

Distal coupler 316 may include a tip pad 346. Tip pad 346 may be formed from a soft-textured silicone or other material that mimics the texture of a real finger and with gripping and provides a softer touch. One embodiment of distal coupler 316 may also include a nail 317, which mimics a natural edged fingernail that may provide scratching and peeling functionalities as well as assist with fine-object manipulation.

Like articulation assemblies 114, 214 of respective prosthetic finger 100, 200, discussed above, articulation assembly 314 is designed for bidirectional articulation. Specifically, assembly 314 and distal coupler 316 rotate laterally relative to the hand via articulation joint 312 of MCP pivot 302, providing prosthetic finger 300 with a first direction of movement about an axis parallel to the z axis and within a plane parallel to the x-y plane. This lateral movement is denoted by arrow A, shown in FIG. 8.

Vertical movement within planes parallel to the x-z plane is denoted by arrow B of FIG. 9. Specifically, hinged connections 324 and 334, which rotatively couple articulation assembly 314 with frame 310 of MCP pivot 302, as well as distal and proximal coordinated pivot points 372, 374, which indirectly and rotatively couple adjustable ring tendon 328 with distal coupler 316, provide multiple rotational connections for movement about numerous axes parallel to the y axis and within planes parallel to the x-z plane. As a result, the user may achieve more lifelike movements of distal coupler 316 that emulate the natural articulation of a finger by moving his or her residual finger laterally (e.g., adducting and/or abducting the residual finger) within ring 238, and/or by moving his or her residual finger vertically within ring 238 to achieve both lateral and vertical articulation of distal coupler 216.

Embodiments of bidirectional biomechanical prosthetic finger 100, 200, 300 are custom designed and individually fitted to accommodate a variety of differing user conditions. In this regard, each finger 100, 200, 300 may be custom manufactured to fit a particular patient or user, providing both custom functionality as well as a mechanical match to the anatomical joint articulation of the user. Design considerations include a number and physiology of joints to be stabilized and other characteristics specific to the individual end user.

To further provide better aesthetics, embodiments of prosthetic finger 100, 200, 300 may be coated with films and/or colorings matched to the user's skin tone/color. An additive manufacturing process (i.e., 3D printing) facilitates this ability to customize the intricacies of the prosthetic design in order to optimize prosthetic finger 100, 200, 300 for each patient.

For additional functionality, embodiments of prosthetic finger 100, 200, 300 may incorporate a touchscreen mechanism (not shown) to allow the user to use prosthetic finger 100, 200, 300 to operate capacitive touchscreens, which react to the body's natural current. The touchscreen mechanism allows the user to direct his or her own body current through distal coupler 116, 216, 316.

Embodiments of prosthetic finger 100, 200, 300 may be formed of any suitable structural material that is non-irritating to human skin and allows the user to operate the brace with comfort and confidence. Exemplary materials include titanium, stainless steel, aluminum, silicone, carbon fiber, nylon, plastic/polymer, wood, rubber, gold, silver, tungsten, flex cable, neoprene, or any other suitable material. In one embodiment, components of prosthetic finger 100, 200, 300 are 3D printed from Duraform EX polymer material.

Using biocompatible materials, various embodiments of prosthetic finger 100, 200, 300 may be applied as an orthopedic implant that may be surgically implanted into a user's finger. This option may be applied for users having injuries that have crushed their finger bones without the ability to heal or be repaired. In these situations, implantable embodiments of biomechanical finger 100, 200, 300 are able to take the place of the user's original bones without the need for amputation.

Once finger 100, 200, 300 (adjusted or otherwise) is in place, the user may utilize his or her natural finger movements. The rotatively coupled components of finger 100, 200, 300 will articulate using the same cognitive process that was previously utilized for the original finger. If a user wears multiple prosthetic fingers 100, 200, 300, each may be individually operated.

Embodiments of the finger assembly 100, 200, 300 described above exhibit numerous unique characteristics and provide a variety of medical benefits. An individual's unique physiology and lifestyle patterns dictate the function and performance expected of his or her hands. Using embodiments of the prosthetic finger assembly described herein, patients may regain independent control of their hands, whether at work or at play. Each device is custom designed, manufactured for a specific individual, and incorporates features that allow for further fine-tuning and adjustment of fit to account for post-manufacturing fluctuations (e.g., shims), enabling the device to fit the user in a manner that allows for a biomechanically driven, low profile, lightweight, highly functioning return to the user's everyday activities, no matter what those activities might entail. A few examples include typing, playing the piano or another instrument, woodworking, and much more.

Embodiments of the biomechanical finger assembly described above are body powered, accommodate bidirectional movement, and feature linked components that articulate when the user simply moves his or her residual finger and/or adjacent fingers. Beyond allowing for a simple, elegant, and streamlined design that offers strength in the lowest possible profile design, employing the user's own biomechanics to drive embodiments of finger 100, 200, 300 provides a host of medical benefits to the user, including reduced swelling of and increased circulation to the residual finger and the hand as a whole, supporting healthy joints in the injured and adjacent fingers.

Figure 11:
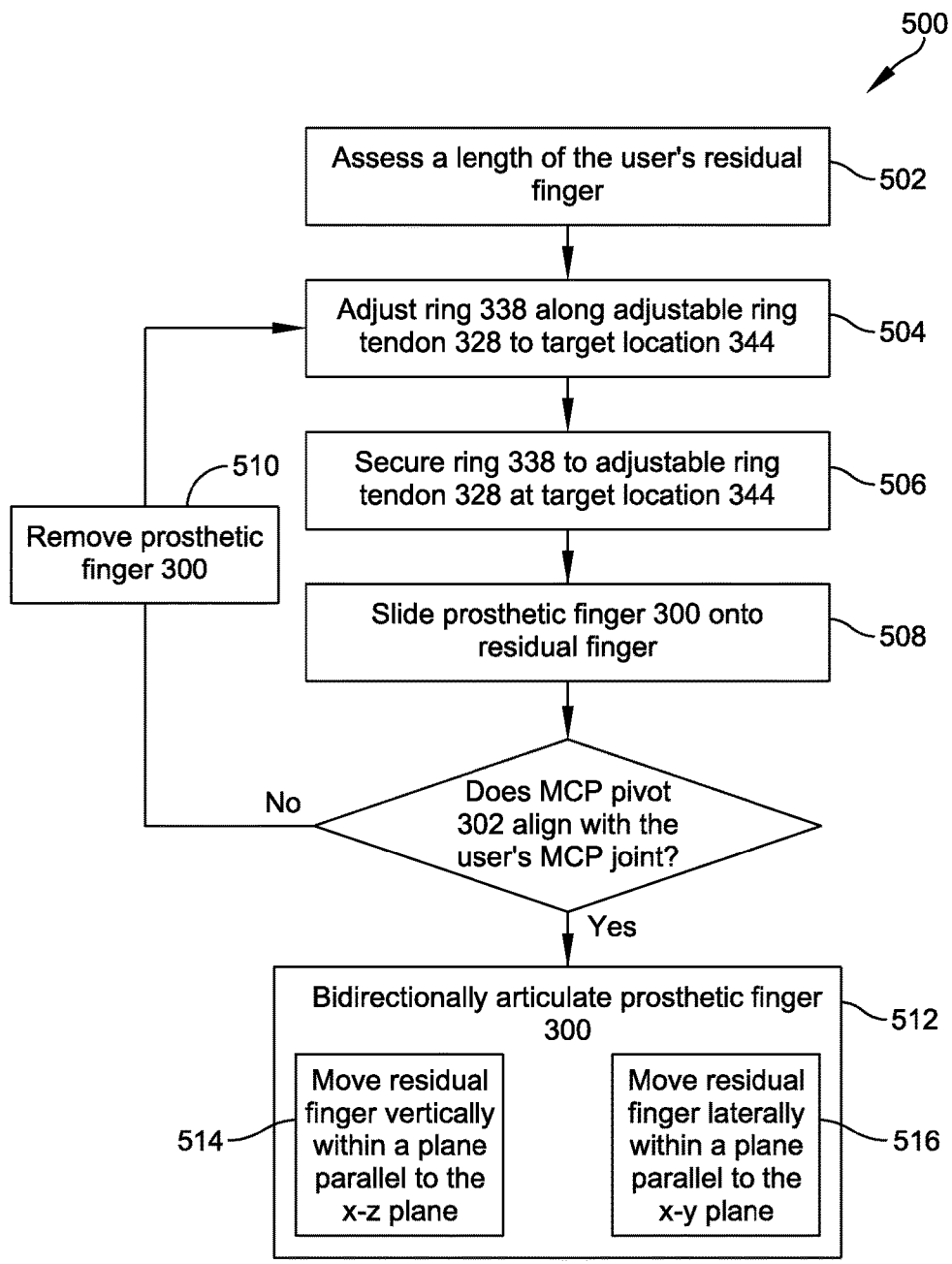
FIG. 11 provides a flow chart depicting an exemplary method of operating the prosthetic finger of FIGS. 8-10.

FIG. 11 provides a flow chart depicting an exemplary method 500 of operation the prosthetic finger assemblies discussed above. For the sake of clarity, method 500 will be described in relation to finger assembly 300, but it should be understood that method 500 applies equally to any prosthetic finger embodiment. Method 500 may begin with assessing a length (502) of the user's residual finger. Based on this length, ring 338 may be adjusted (504) along adjustable ring tendon 328 to target location 344 and secured (506) in place along the longitudinal adjustment mechanism of adjustable ring tendon 328. As discussed above, the longitudinal adjustment mechanism may take any appropriate size, shape, type, and/or configuration that allows ring 338 to be secured at a location along the length of adjustable ring tendon 328 that aligns MCP pivot 302 with the MCP joint of the user.

Once ring 338 has been adjusted and secured, finger assembly 300 may be slid onto the user's residual finger (508), such that ring 338 encircles and retains the residual finger adjacent to target location 344 and the MCP pivot aligns with the user's MCP joint. If MCP pivot 302 does not align with the user MCP joint once ring 338 is fitted about the residual finger, then prosthetic finger 300 may be removed (510) for readjustment (504). If MCP pivot 302 aligns above the user's MCP joint once ring 338 is fitted about the residual finger, then the user may bidirectionally articulate (512) prosthetic finger 300 by moving his or her residual finger vertically (514) within ring 338, thereby causing articulation assembly 314 and distal coupler 316 to articulate within a plane parallel to the x-z plane and about a number of axes parallel to the y axis, and by moving his or her residual finger laterally (516) within ring 338, thereby causing articulation assembly 314 and distal coupler 316 to revolve about MCP pivot 302 within a plane parallel to the x-y plane and about an axis parallel to the z axis.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A biomechanical finger assembly for a user's residual finger, comprising:
    an eccentric metacarpophalangeal (MCP) pivot;
    a distal coupler;
    an adjustable ring tendon having a distal end and a proximal end in opposition to one another, the distal end pivotally attached to the distal coupler and the proximal end pivotally attached to the MCP pivot, the adjustable ring tendon having a longitudinal adjustment mechanism;
    a ring configured to concentrically receive and retain the residual finger, the ring disposed upon the adjustable ring tendon at a target location along the longitudinal adjustment mechanism;
    a proximal rocker having a distal end and a proximal end in opposition to one another, the distal end of the proximal rocker pivotally attached to the distal coupler and the proximal end of the proximal rocker pivotally attached to the MCP pivot; and
    a hand strap configured for attachment to a back of a hand of the user, wherein:
    the adjustable ring tendon together with the proximal rocker are configured to utilize vertical movements of the residual finger within the ring to articulate the distal coupler within a plane parallel to an x-z plane and about one or more axes parallel to a y axis; and
    the MCP pivot is configured to utilize abduction and adduction movements of the residual finger within the ring to articulate the distal coupler within a plane parallel to an x-y plane and about an axis parallel to a z axis, wherein the MCP pivot comprises:
    an anchor plate secured to the hand strap; and
    a frame having a proximal end and a distal end in opposition to one another, the distal end of the frame pivotally attached to the proximal end of the adjustable ring tendon and the proximal end of the proximal rocker, the proximal end of the frame disposed above the anchor plate and pivotally attached to the anchor plate via an articulation joint.

2. The biomechanical finger assembly of claim 1, wherein the articulation joint comprises a pin.

3. The biomechanical finger assembly of claim 1, wherein the longitudinal adjustment mechanism of the adjustable ring tendon comprises a longitudinal adjustment channel having a proximal end and a distal end.

4. The biomechanical finger assembly of claim 3, wherein the target location along the adjustable ring mechanism comprises a location between the proximal and distal ends of the longitudinal adjustment channel that causes the MCP pivot to align with an MCP joint of the user when the residual finger is retained within the ring.

5. A biomechanical finger assembly for a user's residual finger, comprising:
   an eccentric metacarpophalangeal (MCP) pivot;
   a distal coupler;
   an adjustable ring tendon having a distal end and a proximal end in opposition to one another, the distal end pivotally attached to the distal coupler and the proximal end pivotally attached to the MCP pivot, the adjustable ring tendon having a longitudinal adjustment mechanism;
   a ring configured to concentrically receive and retain the residual finger, the ring disposed upon the adjustable ring tendon at a target location along the longitudinal adjustment mechanism; and
   a proximal rocker having a distal end and a proximal end in opposition to one another, the distal end of the proximal rocker pivotally attached to the distal coupler and the proximal end of the proximal rocker pivotally attached to the MCP pivot, wherein:
   the adjustable ring tendon together with the proximal rocker are configured to utilize vertical movements of the residual finger within the ring to articulate the distal coupler within a plane parallel to an x-z plane and about one or more axes parallel to a y axis;
   the MCP pivot is configured to utilize abduction and adduction movements of the residual finger within the ring to articulate the distal coupler within a plane parallel to an x-y plane and about an axis parallel to a z axis;
   the longitudinal adjustment mechanism of the adjustable ring tendon comprises a plurality of adjustment holes between the proximal and distal ends of the tendon; and
   each of the adjustment holes are configured to anchor the ring.

6. The biomechanical finger assembly of claim 5, wherein the target location of the ring along the longitudinal adjustment mechanism comprises a select one of the adjustment holes that causes the MCP pivot to align with an MCP joint of the user when the residual finger is retained within the ring.

7. A bidirectional biomechanically driven finger assembly, comprising:
   a hand strap;
   a metacarpophalangeal (MCP) pivot, comprising:
      an anchor plate having top and bottom surfaces;
      a frame having proximal and distal ends and top and bottom surfaces, the bottom surface of the proximal end of the frame disposed upon the top surface of the anchor plate; and
      an articulation joint, the articulation joint pinning the anchor plate and frame together such that they revolve relative to one another about an axis parallel to a z axis;
   a distal coupler; and
   an adjustable articulation assembly that rotatively couples the MCP pivot and the distal coupler, the adjustable articulation assembly adjusted to receive a residual finger of a user at a target location that causes the MCP pivot to align with an MCP joint of the user, wherein:
   the adjustable articulation assembly is configured to utilize articulation movements of the residual finger within the adjustable articulation assembly to articulate the distal coupler within a plane parallel to an x-z plane and about one or more axes parallel to a y axis;
   the MCP pivot is configured to utilize lateral movements of the residual finger within the adjustable articulation assembly to displace the distal coupler within a plane parallel to an x-y plane and about the axis parallel to the z axis; and
   the bottom surface of the anchor plate is secured to the hand strap such that the MCP pivot is configured to rest above a select MCP joint of the user.

8. A bidirectional biomechanically driven finger assembly, comprising:
   a metacarpophalangeal (MCP) pivot, comprising:
      an anchor plate having top and bottom surfaces;
      a frame having proximal and distal ends and top and bottom surfaces, the bottom surface of the proximal end of the frame disposed upon the top surface of the anchor plate; and
      an articulation joint, the articulation joint pinning the anchor plate and frame together such that they revolve relative to one another about an axis parallel to a z axis;
   a distal coupler; and
   an adjustable articulation assembly that rotatively couples the MCP pivot and the distal coupler, the adjustable articulation assembly adjusted to receive a residual finger of a user at a target location that causes the MCP pivot to align with an MCP joint of the user, wherein:
   the adjustable articulation assembly is configured to utilize articulation movements of the residual finger within the adjustable articulation assembly to articulate the distal coupler within a plane parallel to an x-z plane and about one or more axes parallel to a y axis;
   the MCP pivot is configured to utilize lateral movements of the residual finger within the adjustable articulation assembly to displace the distal coupler within a plane parallel to an x-y plane and about the axis parallel to the z axis; and
   the adjustable articulation assembly comprises:
      an adjustable ring tendon having a distal end and a proximal end in opposition to one another, the distal end of the tendon pivotally attached to the distal coupler and the proximal end of the tendon pivotally attached to the frame of the MCP pivot;
      a ring configured to concentrically receive and retain the residual finger, the ring disposed upon the adjustable ring tendon at the target location; and
      a proximal rocker having a distal end and a proximal end in opposition to one another, the distal end of the proximal rocker pivotally attached to the distal coupler and the proximal end of the proximal rocker pivotally attached to the frame of the MCP pivot.

9. The bidirectional biomechanically driven finger assembly of claim 8, wherein the adjustable ring tendon includes a longitudinal adjustment mechanism.

10. The bidirectional biomechanically driven finger assembly of claim 9, wherein the longitudinal adjustment mechanism of the adjustable ring tendon comprises a longitudinal adjustment channel having a proximal end and a distal end, and wherein the target location is a point between the proximal and distal ends of the longitudinal adjustment channel.

11. The bidirectional biomechanically driven finger assembly of claim 9, wherein the longitudinal adjustment mechanism of the adjustable ring tendon comprises a plurality of adjustment holes, and wherein the target location aligns with a select one of the adjustment holes.

* * * * *